(12) United States Patent
Simonet et al.

(10) Patent No.: US 6,790,823 B1
(45) Date of Patent: Sep. 14, 2004

(54) COMPOSITIONS AND METHODS FOR THE PREVENTION AND TREATMENT OF CARDIOVASCULAR DISEASES

(75) Inventors: Scott Simonet, Thousand Oaks, CA (US); Ildiko Sarosi, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/064,832

(22) Filed: Apr. 23, 1998

(51) Int. Cl.$^7$ .......................... A61K 38/00; C07K 1/00; C07K 14/51; C07K 16/46
(52) U.S. Cl. .............................. 514/2; 514/12; 530/350; 530/387.1; 530/388.24
(58) Field of Search ....................... 514/2, 12; 530/350, 530/387.1, 388.24

(56) References Cited

U.S. PATENT DOCUMENTS

| | | | |
|---|---|---|---|
| 4,179,337 A | 12/1979 | Davis et al. | |
| 4,695,623 A | 9/1987 | Stabinsky | |
| 5,580,722 A | * 12/1996 | Foulkes et al. ................. | 435/6 |

FOREIGN PATENT DOCUMENTS

| WO | WO90/14363 | 11/1990 |
|---|---|---|
| WO | WO97/23614 | 7/1997 |

OTHER PUBLICATIONS

Smithies et al. Gene targeting approaches to complex genetic disease: Atherosclerosis and essential hypertension. Proc. Natl. Acad. Sci. vol. 92 5266–5272 (1995).*
Bronson et al. Altering Mice by Homologous Recombination Using Embryonic Stem Cell. Journal of Biol. Chem. vol. 269/44 27155–27158 (1994).*
Pham et al. Long–range disruption of gene expression by a selectable marker cassette. Proc. Natl. Acad. Sci. vol. 93 13090–13095 (1996).*
Goeddel, *Methods of Enzymology* v. 185, Academic Press (1990).
Haust et al., Am. J. Pathol. 60, 329–346 (1970).
Malik et al., Exp. Hematol. 20: 1028–1035 (1992).
Manologas and Jilka New Eng. J. Med. 332, 305–311 (1995).
Mundy et al. Bone 17, 71S–75S F(1995).
Mundy, J. Bone Min. Res. 8, S505–S510 (1993).
Mundy, J. Cell Biochem. 53. 296–300 (1993).
O'Brien et al. Circulation 92, 2163–2168 (1995).
Pacifici, J. Bone Min. Res. 11, 1043–1051 (1996).
Parhami and Demer, Curr. Opin. Lipidology 8, 312–314 (1997).
Parhami et al. Arterioscler. Thromb. Vasc. Biol. 17, 680–687 (1997).
Parhami et al. J. Atheroscler. Thromb. 3, 90–94 (1996).
Remington's Pharmaceutical Sciences, 18th Ed. (1990, Mack Publishing Co., Easton, PA 18042) pp. 1435–1712.
Roodman, Endocrine Rev. 17, 308–332 (1996).
Sambrook et al. *Molecular Cloning: A Laboratory Manual*, 2nd ed. Cold Spring Harbor Laboratory Press, Cold Spring Harbor, New York (1989).
Simonet et al. Cell 89, 309–319 (1997).
Takahashi et al. Endocrinology 123, 2600–2602 (1988).
Banks et al. Eur. J. Clin. Invest. 24, 813–817 (1994).
Bostrom et al. Am. J. Cardiol. 75, 88B–91B (1995).
Bostrom et al. J. Clin. Invest. 91, 1800–1809 (1993).
Bunting, J. Exp. Med. 8, 365–376 (1906).
Demer, Circulation 92, 2029–2032 (1995).
Erlebacher et al. Cell 80, 371–380 (1995).
Giachelli et al. J. Clin. Invest. 92, 1686–1696 1993).
Bucay et al., Genes and Development 12, 1260–1268 (1998).
Schinke et al., Annals of Medicine 30: 538–541 (1998).

* cited by examiner

*Primary Examiner*—Elizabeth Kemmerer
*Assistant Examiner*—Regina M. DeBerry
(74) *Attorney, Agent, or Firm*—Robert B. Winter; Stuart L. Watt; Ron K. Levy (57) ABSTRACT

Methods and compositions for the prevention and treatment of cardiovascular disease is described. Administration of osteoprotegerin (OPG) in a pharmaceutical composition prevents and treats atherosclerosis and associated cardiovascular diseases.

13 Claims, 4 Drawing Sheets

(4 of 4 Drawing Sheet(s) Filed in Color)

COMPOSITIONS AND METHODS FOR THE PREVENTION AND TREATMENT OF CARDIOVASCULAR DISEASES

FIELD OF THE INVENTION

The invention relates to treatment of cardiovascular diseases. More particularly, the invention involves use of osteoprotegerin (OPG) to treat and prevent cardiovascular diseases associated with occlusion and calcification of blood vessels, such as atherosclerosis.

BACKGROUND OF THE INVENTION

Development and maintenance of the mammalian skeleton involves the regulation and interaction of its component cell types (Erlebacher et al. Cell 80, 371–380 (1995); Marks, Acta Med Dent Helv 2, 141–157 (1997)). Major contributors to skeletal architecture include chondrocytes which form, cartilage, osteoblasts which synthesize and deposit bone matrix, and osteoclasts which resorb bone. Chondrocytes are derived from mesenchymal cells and function to generate an initial cartilage template required for endochondral bone formation. Osteoblasts, derived from mesenchymal osteoprogenitor cells, are located on the surface of bone where they synthesize, transport and arrange the matrix proteins. Osteoclasts are derived from granulocyte-monocyte precursors present in the hematopoietic marrow (Roodman, Endocrine Rev. 17, 308–332 (1996); Mundy, J. Bone Min. Res. 8, S505–S510 (1993); Manologas and Jilka New Eng. J. Med. 332, 305–311 (1995)). After establishing a tight adherence to the bone surface, osteoclasts form resorption zones that are acidified by a specialized structure known as the ruffled border. The ruffled border functions as a secretory conduit where protons and acid proteases are secreted which decalcify and then digest bone matrix. During the process of osteoclast mediated resorption, it is thought that protein factors are elaborated that act as signaling molecules to initiate bone renewal by osteoblasts. Osteoblasts, in turn, can influence osteoclast function through the expression of soluble or membrane bound regulators (Takahashi et al. Endocrinology 123, 2600–2602 (1988)). The coupling between osteoblast and osteoclast functions is critical for skeletal modeling, remodeling, and repair (Mundy, J. Cell Biochem. 53, 296–300 (1993); Mundy et al. Bone 17, 71S–75S F(1995)).

Postmenopausal osteoporosis, the most common bone disease in the developed world, has been causally linked to estrogen loss (for review, see Pacifici, J. Bone Min. Res. 11, 1043–1051 (1996)). Postmenopausal bone loss can be attributed to loss of regulatory control exerted by estrogen on the production of cytokines and other factors that regulate osteoclast development. The resultant shift in the balance of osteoclast and osteoblast activity favors a net loss of bone mass ultimately leading to osteoporosis.

Osteoporosis in human populations has been associated with a higher incidence of arterial calcification, a component of many atherosclerotic lesions (Parhami and Demer, Curr. Opin. Lipidology 8, 312–314 (1997); Banks et al. Eur. J. Clin. Invest. 24, 813–817 (1994); Parhami et al. Arterioscler. Thromb. Vasc. Biol. 17, 680–687 (1997)). Common factors may underlay the pathogenesis of these two diseases. Indeed some arterial calcium mineral deposits appear identical to fully formed lamellar bone, including trabeculae, lacunae, and islands of marrow (Haust and Geer, Am. J. Pathol. 60, 329–346 (1970); Bunting, J. Exp. Med. 8, 365–376 (1906)). Furthermore, calcified arteries have been shown to express several bone matrix proteins, including collagen Type I, matrix GLA protein, osteocalcin, osteonectin and bone morphogenetic protein type 2 (Bostrom et al. J. Clin. Invest. 91, 1800–1809 (1993); O'Brien et al. Circulation 92, 2163–2168 (1995); Giachelli et al. J. Clin. Invest. 92, 1686–1696 1993); Bostrom et al. Am. J. Cardiol. 75, 88B–91B (1995)). These findings have lead to speculation that arterial calcification is an organized, regulated process with cellular and molecular mechanisms similar to organized bone formation (Demer, Circulation 92, 2029–2032 (1995); Parhami et al. J. Atheroscler. Thromb. 3, 90–94 (1996)).

Osteoprotegerin (OPG), a recently identified member of the tumor necrosis factor receptor gene superfamily, is a secreted factor that inhibits osteoclast development both in vitro and in vivo (Simonet et al. Cell 89, 309–319 (1997); PCT Application No. U.S. Ser. No. 96/20621 (WO97/23614) which is hereby incorporated by reference). Transgenic mice overexpressing OPG in the liver, have high levels of OPG protein in their systemic circulation and exhibit a marked increase in bone density (osteopetrosis). In normal mouse embryos, OPG has been localized within cartilage rudiments of developing bones, as well as in the small intestine and the muscular wall of the aorta and several major arteries.

Given the strong correlation between the occurrence of osteoporosis and the onset of conditions which could lead to cardiovascular disease, particularly disease characterized by arterial calcification, and the similarities in the processes for depositing calcium in bone and along the interior of arterial walls, it is an object of the invention to develop pharmaceutical compositions and methods for the concurrent prevention and treatment of osteoporosis and cardiovascular disease. Development of a single therapeutic for the prevention and treatment of both conditions would greatly enhance the longevity and quality of life of affected patients, by reducing the risk of crippling and possibly fatal bone fractures and, at the same time, preventing or retarding conditions which could lead to hypertension, ischemia, heart attacks, and stroke.

Surprisingly, it has been found that loss of OPG in an OPG knockout animal results in calcification of the aorta and renal arteries, which are sites of endogenous OPG expression in normal animals. These findings implicate OPG in the regulation of pathological calcification of arteries such that, when circulating OPG is absent or present at low levels, accumulation of calcium deposits on arterial walls is greatly accelerated. The presence of normal or above normal levels of OPG (such as in transgenic mice expressing OPG) are not associated with vascular calcification.

SUMMARY OF THE INVENTION

The present invention relates to methods and compositions for treating or preventing cardiovascular diseases. The methods comprise administration of a therapeutically effective amount of OPG wherein said amount is sufficient to treat or prevent a cardiovascular disease.

The present invention also relates to OPG compositions useful for treating or preventing cardiovascular disease. OPG compositions are typically pharmaceutically acceptable mixtures suitable for a variety of routes of administration.

DESCRIPTION OF THE FIGURES

The file of this patent contains at least one drawing executed in color. Copies of this patent with color drawings will be provided by the Patent and Trademark Office upon request and payment of the necessary fee.

DETAILED DESCRIPTION OF THE INVENTION

Homozygous OPG$^{-/-}$ knockout mice displayed severe osteoporosis when analyzed by whole body X-ray and by histology. Characterization of bone structure from OPG knockout mice is described in U.S. Ser. No. 08/943,687, now U.S. Pat. No. 6,087,555 hereby incorporated by reference. It was unexpectedly found that both male and female homozygous OPG knockout mice also exhibited marked calcification and intimal proliferation in the aorta and renal artery. These arterial changes were not observed in heterozygous OPG$^{-/+}$ knockout mice, in normal OPG$^{+/+}$ mice, or in transgenic mice exhibiting elevated circulating levels of OPG. OPG+/− mice show bone loss by 6 months of age. Taken together, these observations indicated a role for OPG in preventing or reducing arterial calcification and lessening the risk of atherosclerosis.

OPG Polypeptides

OPG polypeptides of the invention include human OPG or a derivative, truncation, or chemically modified form thereof having at least one of the biological activities of OPG. The amino acid sequence of human OPG is shown in SEQ ID NO:1 and SEQ ID NO:2. A derivative of OPG refers to a polypeptide having an addition, deletion, insertion or substitution of one or more amino acids such that the resulting polypeptide has at least one of the biological activities of OPG. The biological activities of OPG include, but are not limited to, activities involving bone metabolism. In one embodiment, OPG polypeptides have anti-resorptive activity on bone. In another embodiment, OPG polypeptides have activity in reducing or eliminating calcification of arterial walls.

OPG polypeptides will be mature OPG polypeptides having the amino terminal leader sequence of 21 amino acids removed. Polypeptides include residues 22–401 as shown in SEQ ID NO:1 and derivatives thereof having deletions or carboxy-terminal truncations of part or all of amino acids residues 180–401 of OPG; one or more amino acid changes in residues 180–401; deletion of part or all of a cysteine-rich domain of OPG, in particular deletion of the distal (carboxy-terminal) cysteine-rich domain; and one or more amino acid changes in a cysteine-rich domain, in particular in the distal (carboxy-terminal) cysteine-rich domain. In one embodiment, OPG has up to about 216 amino acids deleted from the carboxy terminus. In another embodiment, OPG has up to about 10 amino acids deleted from the mature amino terminus (wherein the mature amino terminus is at residue 22) and, optionally, has up to about 216 amino acids deleted from the carboxy terminus.

Additional OPG polypeptides encompassed by the invention include the following: human [22–180]-Fc fusion, human [22–201]-Fc fusion, human [22–401]-Fc fusion, human [22–185]-Fc fusion, and human [22–194]-Fc fusion. These polypeptides are produced in mammalian host cells, such as CHO or 293 cells, Additional OPG polypeptides encompassed by the invention which are expressed in procaryotic host cells include the following: human met [22–401], met Fc-human[22–401] fusion (Fc region is fused at the amino terminus of the full-length OPG coding sequence) human met[22–401]-Fc fusion (Fc region fused at the carboxy terminus to the full-length OPG sequence), met Fc-human[22–201] fusion, human met[22–201]-Fc fusion, met-Fc-human [22–194], human met[22–194]-Fc, human met[27–401], human met[22–185], human met[22–189], human met[22–194], human met[22–194] (P25A), human met[22–194] (P26A), human met[27–185], human met [27–189], human met [27–194], human met-arg-gly-ser-(his)6[22–401], human met-lys[22–401], human met-(lys) 3-[2$^{2-401}$], human met [22–401]-Fc (P25A), human met [22–401](P25A), human met[22–401](P26A), human met [22–401] (P26D) It is understood that the above OPG polypeptides produced in procaryotic host cells have an amino-terminal methionine residue, if such a residue is not indicated. In specific examples, OPG-Fc fusion polypeptides were produced using a 227 amino acid region of human IgG$_1$-γ1 was used having the sequence as shown in Ellison et al. (Nuc. Acids Res. 10, 4071–4079 (1982)). However, variants of the Fc region of human IgG may also be used.

Analysis of the biological activity of carboxy-terminal OPG truncations fused to the Fc region of human IgG$_1$ indicates that a portion of OPG of about 164 amino acids is required for activity. This region encompasses amino acids 22–185, preferably those in SEQ ID NO:1 and comprises four cysteine-rich domains characteristic of the cysteine-rich domains of tumor necrosis factor receptor (TNFR) extracellular domains.

Using the homology between the cysteine rich domains of OPG and TNFR family members, a three-dimensional model of OPG was generated based upon the known crystal structure of the extracellular domain of TNFR-I (see WO97/23614). This model was used to identify those residues within OPG which may be important for biological activity.

Cysteine residues that are involved in maintaining the structure of the four cysteine-rich domains were identified. The following disulfide bonds were identified in the model: Domain 1: cys41 to cys54, cys44 to cys62, tyr23 and his 66 may act to stabilize the structure of this domain; Domain 2: cys65 to cys80, cys83 to cys98, cys87 to cys105; Domain 3: cys10 to cys118, cys124 to cys142; Domain 4: cys145 to cys160, cys166 to cys185. Residues were also identified which were in close proximity to TNFβ as shown in FIGS. 11 and 12A–12B of WO97/23614. In this model, it is assumed that OPG binds to a corresponding ligand; TNFβ was used as a model ligand to simulate the interaction of OPG with its ligand. Based upon this modeling, the following residues in OPG may be important for ligand binding: glu34, lys43, pro66 to gln91(in particular, pro66, his68, tyr69, tyr70, thr71, asp72, ser73, his76, ser77, asp78, glu79, leu81, tyr82, pro85, val86, lys88, glu90 and gln91), glu153 and ser155.

Alterations in these amino acid residues, either singly or in combination, may alter the biological activity of OPG. For example, changes in specific cysteine residues may alter the structure of individual cysteine-rich domains, whereas changes in residues important for ligand binding may affect physical interactions of OPG with ligand. Structural models can aid in identifying analogs which have more desirable properties, such as enhanced biological activity, greater stability, or greater ease of formulation.

Modifications of OPG polypeptides are encompassed by the invention and include post-translational modifications (e.g., N-linked or O-linked carbohydrate chains, processing of N-terminal or C-terminal ends), attachment of chemical moieties to the amino acid backbone, chemical modifications of N-linked or O-linked carbohydrate chains, and addition of an N-terminal methionine residue as a result of procaryotic host cell expression. The polypeptides may also be modified with a detectable label, such as an enzymatic, fluorescent, isotopic or affinity label to allow for detection and isolation of the protein.

Further modifications of OPG include OPG chimeric or fusion proteins wherein OPG is fused to a heterologous amino acid sequence. The heterologous sequence may be any sequence which allows the resulting fusion protein to retain the activity of OPG. The heterologous sequences include for example, immunoglobulin fusions, such as Fc fusions, which may aid in purification of the protein. A heterologous sequence which promotes association of OPG monomers to form dimers, trimers and other higher multimeric forms is preferred.

In one embodiment, an OPG chimeric protein comprises a fusion of a truncated OPG polypeptide with an Fc region of human IgG. Truncations of OPG may occur at the amino or carboxy termini, or both, and preferably are truncations of up to about 216 amino acids from the carboxy terminus at residue 401. Fusion to an Fc region may occur between the carboxy terminus of an Fc and the amino terminus of an OPG truncated polypeptide, or alternatively between the amino terminus of an Fc region and the carboxy terminus of an OPG truncated polypeptide. Examples of truncated OPG polypeptides fused to an Fc region include residues 22–185, 22–189, 22–194 or 22–201 such as those shown in SEQ ID NO:1 or variants thereof.

The polypeptides of the invention are isolated and purified from other polypeptides present in tissues, cell lines and transformed host cells expressing OPG, or purified from components in cell cultures containing the secreted protein. In one embodiment, the polypeptide is free from association with other human proteins, such as the expression product of a bacterial host cell.

Also provided by the invention are chemically modified derivatives of OPG which may provide additional advantages such as increasing stability and circulating time of the polypeptide, or decreasing immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigeniqity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g. EP 401 384 herein incorporated by reference (coupling PEG to G-CSF), see also Malik et al., Exp. Hematol. 20: 1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydrl groups may also be used as a reactive group for attaching the polyethylene glycol molecule(s). Preferred for therapeutic purposes is attachment at an amino group, such as attachment at the N-terminus or lysine group.

The invention also provides for OPG selectively chemically modified at the amino terminus. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemically modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The invention also provides for an OPG multimer comprising OPG monomers. OPG appears to be active as a multimer (e.g, dimer, trimer or a higher number of monomers). Preferably, OPG multimers are dimers or trimers. OPG multimers may comprise monomers having the amino acid sequence of OPG sufficient to promote multimer formation or may comprise monomers having heterologous sequences such as an antibody Fc region. Analysis of carboxy-terminal deletions of OPG suggest that at least a portion of the region 186–401 is involved in association of OPG polypeptides. Substitution of part or all of the region of OPG amino acids 186–401 with an amino acid sequence capable of self-association is also encompassed by the invention. Alternatively, OPG polypeptides or derivatives thereof may be modified to form dimers or multimers by site directed mutagenesis to create unpaired cysteine residues for interchain disulfide bond formation, by photochemical crosslinking, such as exposure to ultraviolet light, or by chemical crosslinking with bifunctional linker molecules such as bifunctional polyethylene glycol and the like. In one embodiment, OPG multimers are formed by covalent linkage of OPG monomers lacking part or all of the region 186–401 such that association of OPG monomers occurs largely through modification with the linking group.

OPG multimers may be prepared by various chemical crosslinking procedures. OPG monomers may be chemically linked in any fashion that retains or enhances the biological activity of OPG. A variety of chemical crosslinkers may be used depending upon which properties of the protein dimer are desired. For example, crosslinkers may be short and relatively rigid or longer and more flexible, may be biologically reversible, and may provide reduced immunogenicity or longer pharmacokinetic half-life.

OPG molecules are linked through the amino terminus by a two step procedure wherein OPG is chemically modified at the amino terminus to introduce a protected thiol, which after purification is deprotected and used as a point of attachment for site-specific conjugation.through a variety of crosslinkers with a second OPG molecule. Amino-terminal crosslinks include, but are not limited to, a disulfide bond, thioether linkages using short-chain, bis-functional aliphatic crosslinkers, and thioether linkages to variable length, bifunctional polyethylene glycol crosslinkers (PEG "dumbbells"). Also encompassed by PEG dumbbell synthesis of OPG dimers is a byproduct of such synthesis, termed a "monobell". An OPG monobell consists of a monomer coupled to a linear bifunctional PEG with a free polymer terminus. Alternatively, OPG may be crosslinked directly through a variety of amine specific homobifunctional crosslinking techniques which include reagents such as: diethylenetriaminepentaacetic dianhydride (DTPA), p-benzoquinone (pBQ) or bis(sulfosuccinimidyl) suberate (BS$^3$) as well as others known in the art. It is also possible to thiolate OPG directly with reagents such as iminothiolane in the presence of a variety of bifunctional, thiol specific crosslinkers, such as PEG bismaleimide, and achieve dimerization and/or dumbbells in a one-step process.

OPG multimers may also be formed by linking OPG monomers with peptides of varying length. The peptides are chosen to have an amino acid sequence and composition to act as flexible linkers between OPG monomers. Peptide linkers may join monomers in a head-to-head manner (N-terminal to N-terminal or C-terminal to C-terminal) or a head-to-tail manner (N-terminal to C-terminal). Peptide linkers will preferably be about 15–60 amino acids in length.

A method for the purification of OPG from natural sources and from transfected host cells is also included. The purification process may employ one or more standard protein purification steps in an appropriate order to obtain purified protein. The chromatography steps can include ion exchange, gel filtration, hydrophobic interaction, reverse phase, chromatofocusing, affinity chromatography employing an anti-OPG antibody or biotin-streptavidin affinity complex and the like.

Nucleic Acids

Nucleic acid molecules encoding OPG polypeptides of the invention are also provided. The nucleic acid molecules are selected from the following:

a) the nucleic acid sequence as shown in SEQ ID NO:1 or complementary strand thereof;

b) the nucleic acids which hybridize under stringent conditions with the polypeptide-encoding region in SEQ ID NO:1; and c) the nucleic acid sequences which are degenerate to the sequences in (a) and (b).

Conditions for hybridization are generally of high stringency such as 5×SSC, 50% formamide and 42° C. or the equivalent which may be readily obtained by adjusting salt and organic solvent concentrations and temperature. For example, conditions of equivalent stringency may also be used by increasing the temperature of the hybridization or washing step (to a range of 50°–65° C.) and decreasing the salt concentration (to a range of 1 to 0.2×SSC) while omitting organic solvent. Hybridization conditions for nucleic acids are described in further detail in Sambrook et al. *Molecular Cloning: A Laboratory Manual*, 2nd ed. Cold Spring Harbor Laboratory Press, Cold Spring Harbor, N.Y. (1989).

The length of hybridizing nucleic acids of the invention may be variable since hybridization may occur in part or all of the polypeptide-encoding region as shown in SEQ ID NO:1 and may also occur in adjacent noncoding regions. Hybridizing nucleic acids may be shorter or longer in length than the complementary sequence shown in SEQ ID NO:1. Truncated or extended nucleic acids which hybridize to SEQ ID NO:1 may retain one or more of the biological properties of OPG, such as anti-resorptive activity on bone or protection against arterial calcification. The hybridizing nucleic acids may also include adjacent noncoding regions which are 5' and/or 3' to the OPG coding region. The noncoding regions include regulatory regions involved in OPG expression, such as promoters, enhance, translational initiation sites, transcription termination sites and the like.

Also provided by the invention are derivatives of the nucleic acid sequences as shown in SEQ ID NO:1. As used herein, derivatives include nucleic acid sequences having addition, substitution, insertion or deletion of one or more residues such that the resulting sequences encode polypeptides having one or more amino acid residues which have been added, deleted, inserted or substituted and the resulting polypeptide has the activity of OPG, such as anti-resorptive activity on bone or protection against arterial calcification. The nucleic acid derivatives may be naturally occurring, such as by splice variation or polymorphism, or may be constructed using site-directed mutagenesis techniques available to the skilled worker. One example of a naturally occurring variant of OPG is a nucleic acid encoding a lys to asn change at residue 3 within the leader sequence (see WO97/23614). It is anticipated that nucleic acid derivatives will encode amino acid changes in regions of the molecule which are least likely to disrupt biological activity.

In one embodiment, derivatives of OPG include nucleic acids encoding truncated forms of full-length OPG (full-length OPG encompasses residues 22 to 401 of SEQ ID NO:1) having one or more amino acids deleted from the carboxy terminus. Nucleic acids encoding OPG may have up to about 216 amino acids deleted from the carboxy terminus. Optionally, an antibody Fc region may extend from the new carboxy terminus to yield a biologically active OPG-Fc fusion polypeptide, or an Fc region may extend from the amino terminus of the truncated OPG. In preferred embodiments, nucleic acids encode OPG having the amino acid sequence from residues 22–185, 22–189, 22–194 or 22–201 (using numbering in SEQ ID NO:1) and optionally, encoding an Fc region of human IgG.

Also included are nucleic acids encoding truncated forms of OPG having one or more amino acids deleted from the amino terminus. Truncated forms include those lacking part or all the 21 amino acids comprising the leader sequence. Mature OPG lacks all of the 21 amino acid leader sequence. Additionally, the invention provides for nucleic acids encoding OPG having from 1 to 10 amino acids deleted from the mature amino terminus (at residue 22) and, optionally, having from 1 to 216 amino acids deleted from the carboxy terminus (at residue 401). Optionally, the nucleic acids may encode a methionine residue at the amino terminus.

Examples of the nucleic acids of the invention include cDNA, genomic DNA, synthetic DNA and RNA. cDNA is obtained from libraries prepared from mRNA isolated from various tissues expressing OPG. In humans, tissue sources for OPG include kidney, liver, placenta and heart. Genomic DNA encoding OPG is obtained from genomic libraries which are commercially available from a variety of species. Synthetic DNA is obtained by chemical synthesis of overlapping oligonucleotide fragments followed by assembly of the fragments to reconstitute part or all of the coding region and flanking sequences (see U.S. Pat. No. 4,695,623 describing the chemical synthesis of interferon genes). RNA is obtained most easily by procaryotic expression vectors which direct high-level synthesis of MRNA, such as vectors using T7 promoters and RNA polymerase.

Vectors and Host Cells

Expression vectors containing nucleic acid sequences encoding OPG, host cells transformed with said vectors and methods for the production of OPG are also provided by the invention. An overview of expression of recombinant proteins is found in *Methods of Enzymology* v. 185, Goeddel, D. V. ed. Academic Press (1990).

Host cells for the production of OPG include procaryotic host cells, such as *E. coli*, yeast, plant, insect and mammalian host cells. *E. coli* strains such as HB101 or JM101 are suitable for expression. Preferred mammalian host cells include COS, CHOd-, 293, CV-1, 3T3, baby hamster kidney (BHK) cells and others. Mammalian host cells are preferred when post-translational modifications, such as glycosylation and polypeptide processing, are important for OPG activity. Mammalian expression allows for the production of secreted polypeptides which may be recovered from the growth medium.

Vectors for the expression of OPG contain at a minimum sequences required for vector propagation and for expression of the cloned insert. These sequences include a replication origin, selection marker, promoter, ribosome binding site, enhancer sequences, RNA splice sites and transcription termination site. Vectors suitable for expression in the aforementioned host cells are readily available and the nucleic acids of the invention are inserted into the vectors using standard recombinant DNA techniques. Vectors for tissue-specific expression of OPG are also included. Such vectors include promoters which function specifically in liver, kidney or other organs for production in mice, and viral vectors for the expression of OPG in targeted human cells.

Using an appropriate host-vector system, OPG is produced recombinantly by culturing a host cell transformed with an expression vector containing nucleic acid sequences encoding OPG under conditions such that OPG is produced, and isolating the product of expression. OPG is produced in the supernatant of transfected mammalian cells or in inclusion bodies of transformed bacterial host cells. OPG so produced may be purified by procedures known to one skilled in the art as described below. The expression of OPG in mammalian and bacterial host systems is described in WO97/23614. Expression vectors for mammalian hosts are exemplified by plasmids such as pDSRa described in WO90/14363. Expression vectors for bacterial host cells are exemplified by plasmids pAMG21 and pAMG22-His described in WO97/23614. It is anticipated that the specific plasmids and host cells described are for illustrative purposes and that other available plasmids and host cells could also be used to express the polypeptides.

The invention also provides for expression of OPG from endogenous nucleic acids by in vivo or ex vivo recombination events. One strategy involves activation of a normally silent endogenous OPG gene by introduction of exogenous regulatory sequences (e.g. promoters or enhancers) capable of directing the expression of OPG from the endogenous gene, or from a variant gene thereof which is present in the host genome or is generated by the introduction of exogenous sequences. Typically, exogenous sequences are carried on vectors capable of homologous recombination with the host genome. In addition, endogenous or exogenous regulatory sequences capable of directing OPG production may be activated or stimulated to express OPG upon exposure to certain activating or stimulating factors for transcription and/or translation.

OPG Pharmaceutical Compositions

OPG pharmaceutical compositions typically include a therapeutically effective amount of OPG protein product in admixture with one or more pharmaceutically and physiologically acceptable formulation materials. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution or other materials common in compositions for parenteral administration. Neutral buffered saline or saline mixed with serum albumin are further exemplary vehicles.

The primary solvent in a vehicle may be either aqueous or non-aqueous in nature. In addition, the vehicle may contain other pharmaceutically-acceptable excipients for modifying or maintaining the pH, osmolarity, viscosity, clarity, color, sterility, stability, rate of dissolution, or odor of the formulation. Similarly, the vehicle may contain still other pharmaceutically-acceptable excipients for modifying or maintaining the stability, rate of dissolution, or rate of release of OPG. Such excipients are those substances usually and customarily employed to formulate dosages for parenteral administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or in a form, e.g., lyophilized, requiring reconstitution prior to administration.

The optimal pharmaceutical formulation will be determined by one skilled in the art depending upon the route of administration and desired dosage. See for example, *Remington's Pharmaceutical Sciences*, 18th Ed. (1990, Mack Publishing Co., Easton, Pa. 18042) pages 1435–1712 the disclosure of which is hereby incorporated by reference.

Other effective administration forms, such as parenteral slow-release formulations, inhalant mists, orally active formulations, or suppositories, are also envisioned. In one embodiment, OPG pharmaceutical compositions are formulated for parenteral administration. Such parenterally administered therapeutic compositions are typically in the form of a pyrogen-free, parenterally acceptable aqueous solution comprising OPG in a pharmaceutically acceptable vehicle. One preferred vehicle is physiological saline.

Compositions for sustained release and/or delivery of OPG comprise OPG polypeptides modified with water soluble polymers as described above to increase solubility or stability. Compositions may also comprise incorporation of OPG into liposomes, microemulsions, micelles or vesicles for controlled delivery over an extended period of time. Specifically, OPG compositions may comprise incorporation into polymer matricies such as hydrogels, silicones, polyethylenes, ethylene-vinyl acetate copolymers, or biodegradable polymers. Examples of hydrogels include polyhydroxyalkylmethacrylates (p-HEMA), polyacrylamide, polymethacrylamide, polyvinylpyrrolidone; polyvinyl alcohol and various polyelectrolyte complexes. Examples of biodegradable polymers include polylactic acid (PLA), polyglycolic acid (PGA), copolymers of PLA and PGA, polyamides and copolymers of polyamides and polyesters. Other controlled release formulations include microcapsules, microspheres, macromolecular complexes and polymeric beads which may be administered by injection. Hylauronic acid may also be used, and this may have the effect of promoting sustained duration in the circulation. Such compositions may influence the physical state, stability, rate of in vivo release, and rate of in vivo clearance of the present proteins and derivatives.

It is also contemplated that certain formulations containing OPG are to be administered orally. OPG which is administered in this fashion may be encapsulated and may be formulated with or without those carriers customarily used in the compounding of solid dosage forms. The capsule may designed to release the active portion of the formulation at the point in the gastrointestinal tract when bioavailability is maximized and pre-systemic degradation is minimized. Additional excipients may be included to facilitate absorption. Diluents, flavorings, low melting point waxes, vegetable oils, lubricants, suspending agents, tablet disintegrating agents, and binders may also be employed.

Administration of OPG

OPG polypeptides may be administered parenterally via a subcutaneous, intramuscular, intravenous, transpulmonary, or transdermal route. To achieve the desired dose of OPG, repeated daily or less frequent injections may be administered. The frequency of dosing will depend on the pharmacokinetic parameters of the OPG polypeptide as formulated, and the route of administration.

Regardless of the manner of administration, the specific dose is typically calculated according to body weight or body surface area. Further refinement of the calculations necessary to determine the appropriate dosage for treatment involving each of the above mentioned formulations is routinely made by those of ordinary skill in the art, especially in light of the dosage information and assays disclosed herein. Appropriate dosages may be ascertained through use of the established assays for determining dosages utilized in conjunction with appropriate dose-response data. The final dosage regimen involved in a method of treating a specific condition will be determined by the attending physician, considering various factors which modify the action of drugs, e.g., the age, condition, body weight, sex and diet of the patient, the severity of any infection, time of administration and other clinical factors. In one embodiment, the dose range for an Fc-OPG fusion protein, wherein the carboxy terminus of an Fc region is attached to the amino-terminal residue of a truncated OPG polypeptide (e.g., FC-OPG[22–194]), is about 10 $\mu$g/kg to about 10 mg/kg.

OPG gene therapy in vivo is also envisioned wherein a nucleic acid sequence encoding OPG, a derivative thereof, or an OPG chimeric protein is introduced directly into the patient. For example, a nucleic acid sequence encoding an OPG polypeptide is introduced into target cells via local injection of a nucleic acid construct with or without an appropriate delivery vector, such as an adeno-associated virus vector. Alternative viral vectors include, but are not limited to, retrovirus, adenovirus, herpes simplex. virus and papilloma virus vectors. Physical transfer may be achieved in vivo by local injection of the desired nucleic acid construct or other appropriate delivery vector containing the desired nucleic acid sequence, liposome-mediated transfer, direct injection (naked DNA), receptor-mediated transfer (ligand-DNA complex), or microparticle bombardment (gene gun).

Atherosclerosis causes most degenerative arterial disease and calcification of the arterial wall typically occurs in clinically significant lesions. Narrowing and occlusion of the artery are the most common features of the disease although the strength of the arterial wall may also be compromised from loss of elastin and collagen. Consequences of arterial occlusion include dissection, aneurysms, ischemia, thrombosis, and acute and chronic cardiac diseases. In many instances, surgical or angioplastic treatments are required and, while effective, such treatments are necessarily invasive, do not prevent occlusion at other arterial sites, and in some cases may need to be repeated at the original sites (for example, in restenosis).

OPG may be used to prevent or treat atherosclerosis and Mockenberg's arteriosclerosis (medial calcific sclerosis), and other, conditions characterized by arterial calcification. OPG may be administered alone or in combination with other drugs for treating atherosclerosis, such as anti-hypertensive drugs and cholesterol lowering drugs. Anti-hypertensive drugs include diuretics, $\alpha$-adrenergic blocking drugs, $\beta$-adrenergic blocking drugs, calcium entry blocking drugs, angiotensin converting enzyme inhibitors and vasodilators. Cholesterol lowering drugs which reduce levels of low density lipoprotein (LDL) cholesterol include bile acid sequestrants, HMG-CoA reducatse inhibitors, fibric acid derivatives and nicotinic acid. OPG may also be administered with anti-resorptive agents which may exhibit cardiovascular benefit, such as hormones (estrogens), vitamin D and vitamin D derivatives, and selective estrogen receptor modulators (SERMs), such as raloxifene (EVISTA). In addition, OPG may be administered in conjunction with surgical and angioplastic treatments, such as arterial prosthesis and balloon angioplasty.

The invention will be more fully understood by reference to the following examples. These examples are not to be construed in any way as limiting the scope of this invention.

EXAMPLE 1

OPG Expression Analyzed by in situ Hybridization

Preparation of embryos and tissues for in situ hybridization experiments and preparation of radioactively labeled oligonucleotide probes for detecting OPG MRNA levels have been described previously in Simonet et al. supra. Localization of high levels of OPG mRNA in the incipient part of the aorta in 18.5 day mouse embryo is shown in FIGS. 1A–1D. OPG expression in the adult rat is also apparent in the smooth muscle wall of the renal artery as shown in FIGS. 2A–2E.

EXAMPLE 2

Preparation of OPG Knockout Mice

Procedures for preparing OPG Knockout Mice including construction of vectors for targeting OPG sequences to the mouse genome and introduction of said vectors into mouse embryos are described in U.S. Ser. No. 08/943,687 now U.S. Pat. No. 6,087,555 which is hereby incorporated by reference.

EXAMPLE 3

Phenotypic Analysis of OPG Knockout Mice

Groups of homozygous OPG knockout mice (OPG$^{-/-}$), heterozygous knockout mice (OPG$^{-/-}$) and control mice (OPG$^{+/-}$) were necropsied at e18 and 7 day, 14 day, 60 day and 180 day postnatal. Radiography was performed prior to gross dissection. Serum from the mice was analyzed for clinical chemistries and full hematology. Total body and major organs were weighed and fixed in formalin.

A summary of the mice undergoing necropsy is shown in Table 1.

TABLE 1

| Wild types (+/+) | Heterozgotes (+/−) | Homozygotes (−/−) |
| --- | --- | --- |
| 1–34 Male | 1–28 Male | 1–27 Male |
| 1–37 Male | 1–29 Male | 1–26 Male ♦ |
| 1–45 Male | 1–35 Male | 1–38 Male ▼ |

TABLE 1-continued

| Wild types (+/+) | Heterozgotes (+/−) | Homozygotes (−/−) |
| --- | --- | --- |
| 1–25 Male | 1–36 Male | 77 Female |
| 81 Female | 1–46 Male | 80 Female |
| 82 Female | 75 Female | 86 Female |
| 83 Female | 76 Female | |
| | 78 Female | |

♦ OPG$^{-/-}$ Mouse 1–26 was the runt of the litter, about half the size of a normal mouse. It became moribund and died shortly before the scheduled sacrifice, it displayed the signs of respiratory insufficiency shortly before dying. Blood for hematology and serum chemistries was drawn immediately after death by cardiac puncture and a regular necropsy was performed.

▼ OPG$^{-/-}$ Mouse 1–38 was placed in one cage with OPG−/− mouse 1–27 in preparation for the procedures and died within the last 1 hour prior to sacrifice, no blood could be collected for testing. The rest of the autopsy was performed as usual and organs submitted for histology.

Analysis and results of bone morphology, histology and density, and hematology and serum chemistry parameters in OPG knockout mice have been reported in U.S. Ser. No. 08/943,687 now U.S. Pat. No. 6,087,555.

Figure 1A:
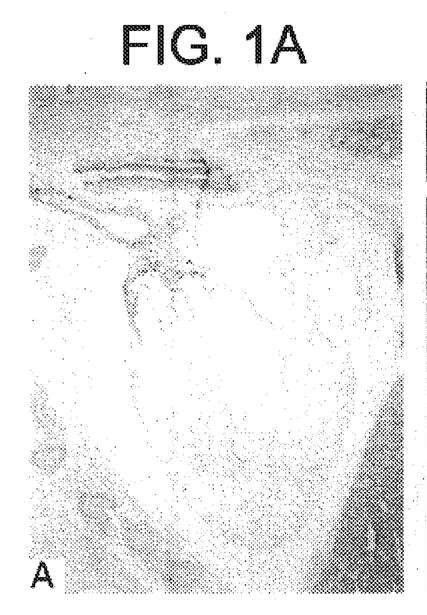
FIGS. 1A–D. In situ hybridization analysis of OPG expression on frozen sections of E17 rat embryo heart (Panels A and B) and adult rat renal artery (Panels C and D). On light microscopy the presence of OPG mRNA is seen as dark grains over the aorta, the background stain is Methyl green (A). On dark field microscopy of the same specimen strong OPG mRNA expression is seen over the ribs and the aorta (B). Somewhat weaker signal is present in the renal artery of the adult rat on light and dark field microscopy (C and D, respectively).
Figure 1B:
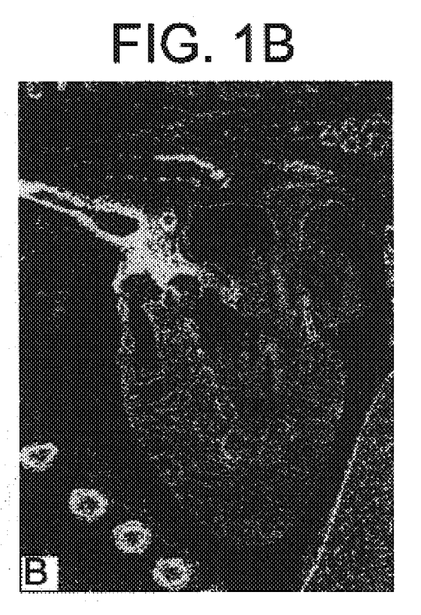
Figure 1C:
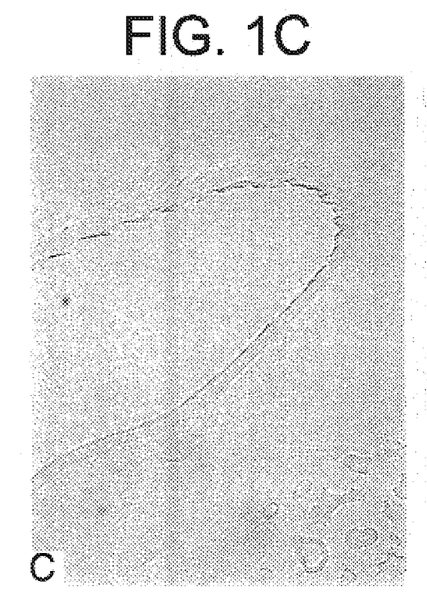
Figure 1D:
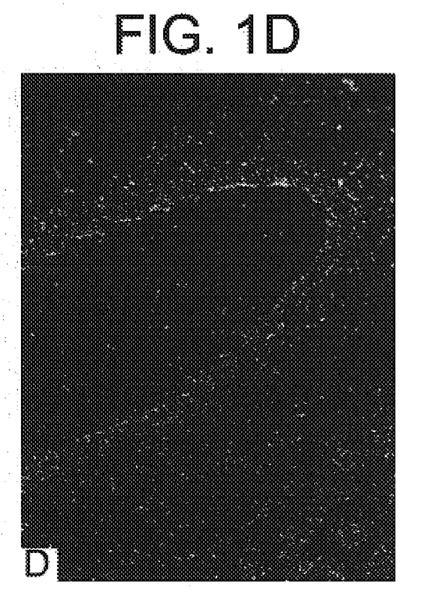
Figure 2A:
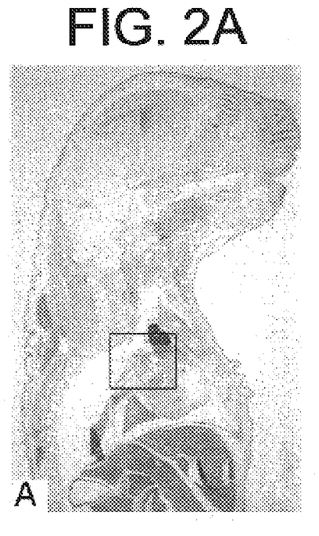
FIGS. 2A–E. In situ hybridization analysis of OPG expression on formalin fixed sections of E20.5 rat embryo. On light microscopy the presence of OPG RNA is seen as dark grains over the aorta, the background stain is hemalaun (Panels A, B and D). On dark field microscopy of the same specimen strong OPG mRNA expression is seen over the aorta. (Panels C and E) E20.5 rat embryo, ½× magnification, section stained with hematoxylin and eosin (A); 4×, H and E (B); 4× (C); 10×, H and E (D); 10× (E).
Figure 2B:
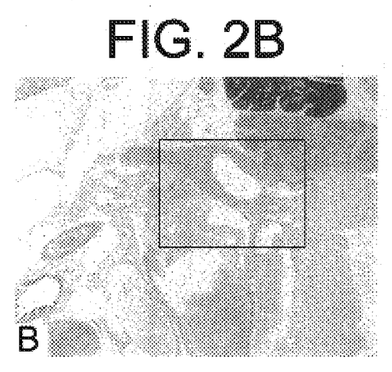
Figure 2C:
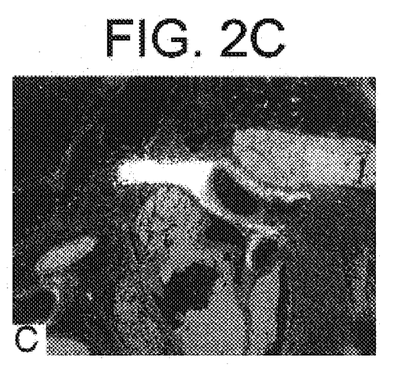
Figure 2D:
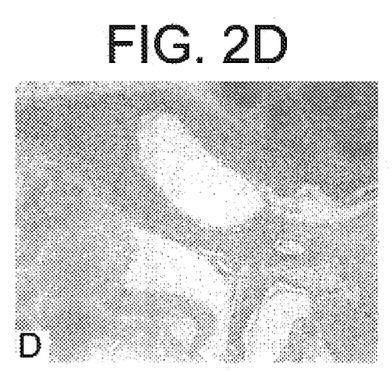
Figure 2E:
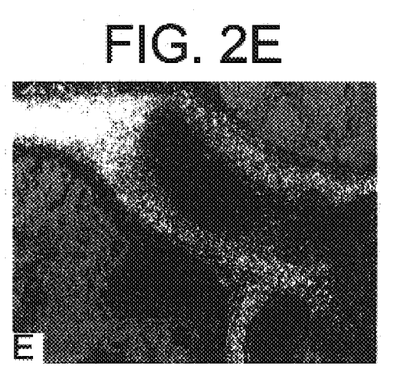
Figure 3A:
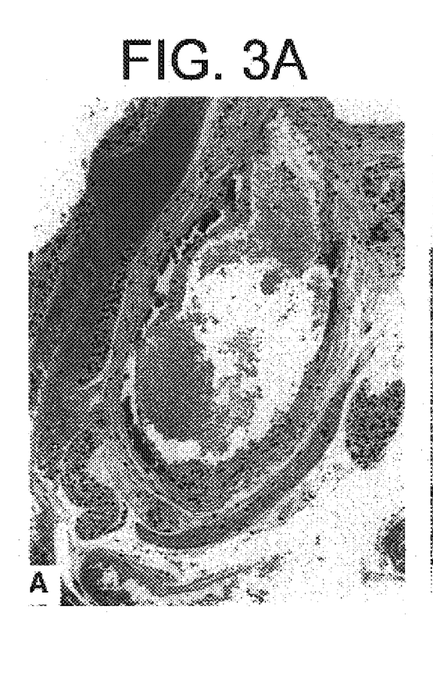
FIGS. 3A–D. Arterial calcification in male OPG$^{-/-}$ mice. OPG$^{-/-}$ mouse #26 has calcification and intimal proliferation in the descending aorta (Panel A) and renal artery (Panel B). OPG$^{-/-}$ mouse #38 has pronounced calcification in the bulb of the aorta (Panel C). The massive subintimal proliferation could be the consequence of a dissection of the wall of the aorta and subsequent bleeding into the space between the layers of the aortic wall. Aneurysm formation and dissection of the wall of the aorta is a common complication of severe arteriosclerosis. There is severe calcification as well as intimal and medial proliferation in the renal artery (Panel D).
Figure 3B:
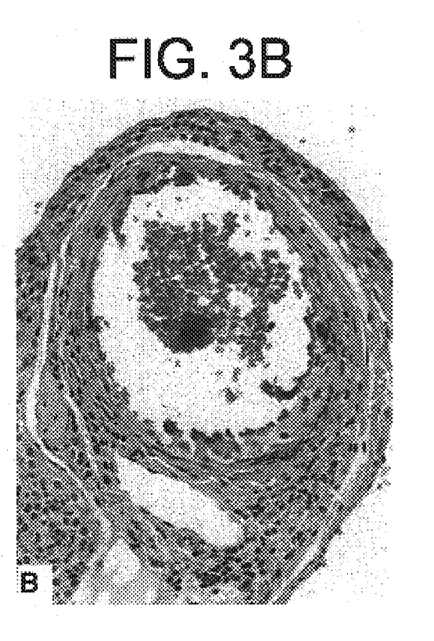
Figure 3C:
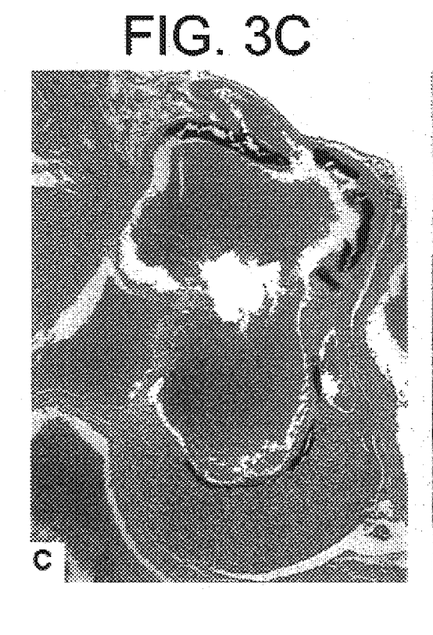
Figure 3D:
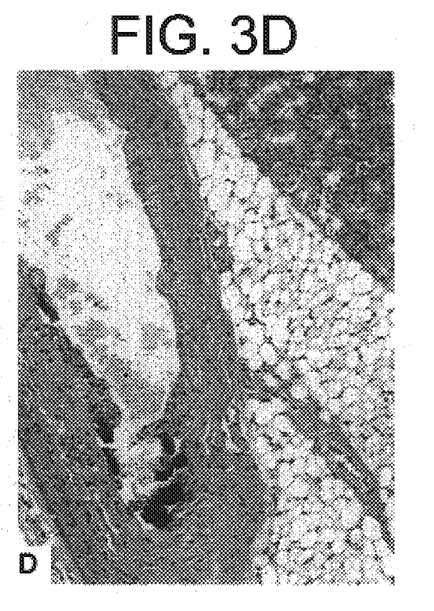

Two of the three male OPG$^{-/-}$ mice had arterial changes. In the heart of Mouse #26 extensive severe subendocardial calcinosis was present. Intimal proliferation and calcifications could be detected in the aorta (FIG. 3A) and renal artery (FIG. 3B). Serum calcium was elevated to 11 versus 8.8±0.17 in the OPG$^{-/-}$ group. OPG$^{-/-}$ Mouse #38—had intimal proliferation and subintimal chronic granulation tissue in the initial part of the aorta (FIG. 3C) and in the renal artery (FIG. 3D). Serum calcium value was not available.

Figure 4A:
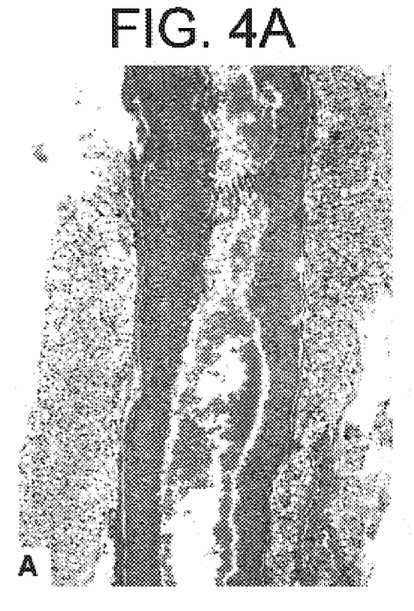
FIGS. 4A–D. Arterial calcification in female OPG$^{-/-}$ mice. The aorta of wild type mouse #82 is shown as negative control (Panel A). OPG$^{-/-}$ mouse #86 has several calcified lesions in the abdominal aorta (Panel B). OPG$^{-/-}$ mouse #77 has several calcified lesions in the abdominal aorta (Panel D) and in several smaller branches (Panel C).
Figure 4B:
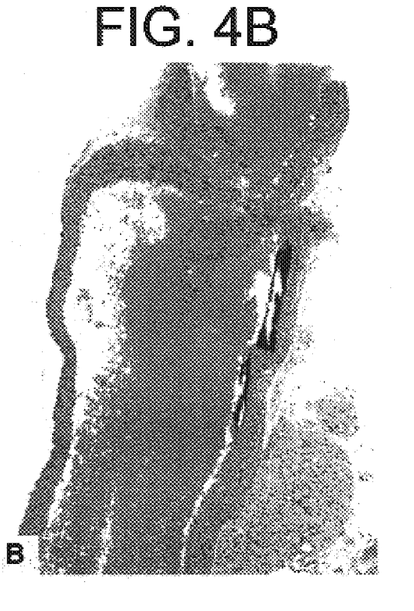
Figure 4C:
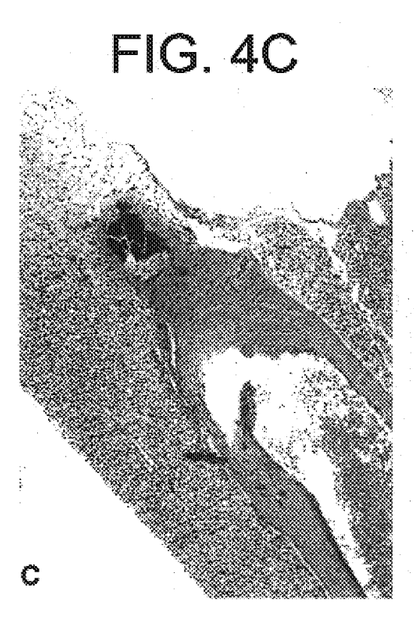
Figure 4D:
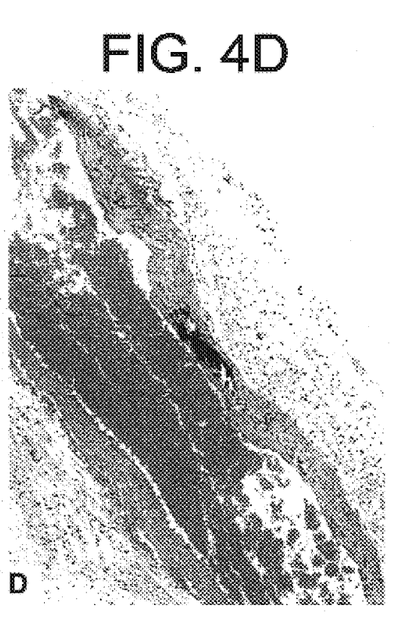

Two of three female OPG$^{-/-}$ mice had calcifications and intimal proliferation in the aorta and renal artery (FIGS. 4B, 4C and 4D), serum calcium values were within the normal range. The third female OPG mouse displayed osteoporosis in the bone, had normal calcium levels and no arterial changes.

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. A method of reducing the incidence of arterial calcification in a patient at risk for arterial calcification comprising administering to said patient a therapeutically effective amount of osteoprotegerin (OPG) in a pharmaceutical composition.

2. The method of claim 1 wherein the arterial calcification is associatd with atherosclerosis or Monckenberg's arteriosclerosis.

3. The method of claim 1 further comprising administering a therapeutically effective amount of a cholesterol-lowering drug.

4. The method of claim 1 wherein osteoprotegerin is administered prior to, concurrent with, or after the onset of cardiovascular disease.

5. The method of claim 1 wherein osteoprotegerin is administered in conjunction with surgical or angioplastic treatment.

6. The method of claim 1 wherein osteoprotegerin is a truncated OPG polypeptide.

7. The method of claim 6 wherein the truncated polypeptide has up to about 216 amino acids deleted from the carboxy terminus as shown in SEQ ID NO:2.

8. The method of claim 7 wherein the truncated OPG polypeptide is a covalently linked multimer.

9. The method of claim 1 wherein osteoprotegerin comprises a chimeric polypeptide comprising a truncated OPG polypeptide fused to an Fc region from human IgG.

10. The method of claim 9 wherein the carboxy terminus of the Fc region is fused to the amino terminus of the truncated OPG polypeptide.

11. The method of claim 9 wherein the amino terminus of the Fc region is fused to the carboxy terminus of the truncated OPG polypeptide.

12. The method of claim 10 or 11 wherein the truncated OPG polypeptide comprises residues 22–185, 22–189, 22–194, or 22–201 as shown in SEQ ID NO:2.

13. The method of claim 1 wherein osteoprotegerin comprises residues 22–401 as shown in SEQ ID NO:2.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1355 base pairs
      (B) TYPE: nucleic acid
      (C) STRANDEDNESS: single
      (D) TOPOLOGY: linear    (ii) MOLECULE TYPE: cDNA    (ix) FEATURE:
      (A) NAME/KEY: CDS
      (B) LOCATION: 94..1297

(xi) SEQUENCE DESCRIPTION: SEQ ID NO:1:

```
GTATATATAA CGTGATGAGC GTACGGGTGC GGAGACGCAC CGGAGCGCTC GCCCAGCCGC       60

CGCTCCAAGC CCCTGAGGTT TCCGGGGACC ACA ATG AAC AAG TTG CTG TGC TGC      114
                                    Met Asn Lys Leu Leu Cys Cys
                                     1               5

GCG CTC GTG TTT CTG GAC ATC TCC ATT AAG TGG ACC ACC CAG GAA ACG       162
Ala Leu Val Phe Leu Asp Ile Ser Ile Lys Trp Thr Thr Gln Glu Thr
         10                  15                  20

TTT CCT CCA AAG TAC CTT CAT TAT GAC GAA GAA ACC TCT CAT CAG CTG       210
Phe Pro Pro Lys Tyr Leu His Tyr Asp Glu Glu Thr Ser His Gln Leu
     25                  30                  35

TTG TGT GAC AAA TGT CCT CCT GGT ACC TAC CTA AAA CAA CAC TGT ACA       258
Leu Cys Asp Lys Cys Pro Pro Gly Thr Tyr Leu Lys Gln His Cys Thr
 40                  45                  50                  55

GCA AAG TGG AAG ACC GTG TGC GCC CCT TGC CCT GAC CAC TAC TAC ACA       306
Ala Lys Trp Lys Thr Val Cys Ala Pro Cys Pro Asp His Tyr Tyr Thr
                 60                  65                  70

GAC AGC TGG CAC ACC AGT GAC GAG TGT CTA TAC TGC AGC CCC GTG TGC       354
Asp Ser Trp His Thr Ser Asp Glu Cys Leu Tyr Cys Ser Pro Val Cys
             75                  80                  85

AAG GAG CTG CAG TAC GTC AAG CAG GAG TGC AAT CGC ACC CAC AAC CGC       402
Lys Glu Leu Gln Tyr Val Lys Gln Glu Cys Asn Arg Thr His Asn Arg
         90                  95                 100

GTG TGC GAA TGC AAG GAA GGG CGC TAC CTT GAG ATA GAG TTC TGC TTG       450
Val Cys Glu Cys Lys Glu Gly Arg Tyr Leu Glu Ile Glu Phe Cys Leu
     105                 110                 115

AAA CAT AGG AGC TGC CCT CCT GGA TTT GGA GTG GTG CAA GCT GGA ACC       498
Lys His Arg Ser Cys Pro Pro Gly Phe Gly Val Val Gln Ala Gly Thr
120                 125                 130                 135

CCA GAG CGA AAT ACA GTT TGC AAA AGA TGT CCA GAT GGG TTC TTC TCA       546
Pro Glu Arg Asn Thr Val Cys Lys Arg Cys Pro Asp Gly Phe Phe Ser
                 140                 145                 150

AAT GAG ACG TCA TCT AAA GCA CCC TGT AGA AAA CAC ACA AAT TGC AGT       594
Asn Glu Thr Ser Ser Lys Ala Pro Cys Arg Lys His Thr Asn Cys Ser
             155                 160                 165

GTC TTT GGT CTC CTG CTA ACT CAG AAA GGA AAT GCA ACA CAC GAC AAC       642
Val Phe Gly Leu Leu Leu Thr Gln Lys Gly Asn Ala Thr His Asp Asn
         170                 175                 180

ATA TGT TCC GGA AAC AGT GAA TCA ACT CAA AAA TGT GGA ATA GAT GTT       690
Ile Cys Ser Gly Asn Ser Glu Ser Thr Gln Lys Cys Gly Ile Asp Val
     185                 190                 195

ACC CTG TGT GAG GAG GCA TTC TTC AGG TTT GCT GTT CCT ACA AAG TTT       738
Thr Leu Cys Glu Glu Ala Phe Phe Arg Phe Ala Val Pro Thr Lys Phe
200                 205                 210                 215

ACG CCT AAC TGG CTT AGT GTC TTG GTA GAC AAT TTG CCT GGC ACC AAA       786
Thr Pro Asn Trp Leu Ser Val Leu Val Asp Asn Leu Pro Gly Thr Lys
                 220                 225                 230

GTA AAC GCA GAG AGT GTA GAG AGG ATA AAA CGG CAA CAC AGC TCA CAA       834
Val Asn Ala Glu Ser Val Glu Arg Ile Lys Arg Gln His Ser Ser Gln
             235                 240                 245

GAA CAG ACT TTC CAG CTG CTG AAG TTA TGG AAA CAT CAA AAC AAA GCC       882
Glu Gln Thr Phe Gln Leu Leu Lys Leu Trp Lys His Gln Asn Lys Ala
         250                 255                 260

CAA GAT ATA GTC AAG AAG ATC ATC CAA GAT ATT GAC CTC TGT GAA AAC       930
Gln Asp Ile Val Lys Lys Ile Ile Gln Asp Ile Asp Leu Cys Glu Asn
     265                 270                 275

AGC GTG CAG CGG CAC ATT GGA CAT GCT AAC CTC ACC TTC GAG CAG CTT       978
Ser Val Gln Arg His Ile Gly His Ala Asn Leu Thr Phe Glu Gln Leu
280                 285                 290                 295
```

```
CGT AGC TTG ATG GAA AGC TTA CCG GGA AAG AAA GTG GGA GCA GAA GAC      1026
Arg Ser Leu Met Glu Ser Leu Pro Gly Lys Lys Val Gly Ala Glu Asp
                    300                 305                 310

ATT GAA AAA ACA ATA AAG GCA TGC AAA CCC AGT GAC CAG ATC CTG AAG      1074
Ile Glu Lys Thr Ile Lys Ala Cys Lys Pro Ser Asp Gln Ile Leu Lys
                315                 320                 325

CTG CTC AGT TTG TGG CGA ATA AAA AAT GGC GAC CAA GAC ACC TTG AAG      1122
Leu Leu Ser Leu Trp Arg Ile Lys Asn Gly Asp Gln Asp Thr Leu Lys
                330                 335                 340

GGC CTA ATG CAC GCA CTA AAG CAC TCA AAG ACG TAC CAC TTT CCC AAA      1170
Gly Leu Met His Ala Leu Lys His Ser Lys Thr Tyr His Phe Pro Lys
345                 350                 355

ACT GTC ACT CAG AGT CTA AAG AAG ACC ATC AGG TTC CTT CAC AGC TTC      1218
Thr Val Thr Gln Ser Leu Lys Lys Thr Ile Arg Phe Leu His Ser Phe
360                 365                 370                 375

ACA ATG TAC AAA TTG TAT CAG AAG TTA TTT TTA GAA ATG ATA GGT AAC      1266
Thr Met Tyr Lys Leu Tyr Gln Lys Leu Phe Leu Glu Met Ile Gly Asn
                380                 385                 390

CAG GTC CAA TCA GTA AAA ATA AGC TGC TTA T AACTGGAAAT GGCCATTGAG      1317
Gln Val Gln Ser Val Lys Ile Ser Cys Leu
                395                 400

CTGTTTCCTC ACAATTGGCG AGATCCCATG GATGATAA                            1355

(2) INFORMATION FOR SEQ ID NO:2:

(i) SEQUENCE CHARACTERISTICS:
        (A) LENGTH: 401 amino acids
        (B) TYPE: amino acid
        (D) TOPOLOGY: linear (ii) MOLECULE TYPE: protein (xi) SEQUENCE DESCRIPTION: SEQ ID NO:2:

Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
                20                  25                  30

Glu Glu Thr Ser His Gln Leu Leu Cys Asp Lys Cys Pro Pro Gly Thr
            35                  40                  45

Tyr Leu Lys Gln His Cys Thr Ala Lys Trp Lys Thr Val Cys Ala Pro
        50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
                100                 105                 110

Leu Glu Ile Glu Phe Cys Leu Lys His Arg Ser Cys Pro Pro Gly Phe
            115                 120                 125

Gly Val Val Gln Ala Gly Thr Pro Glu Arg Asn Thr Val Cys Lys Arg
        130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190
```

-continued

```
Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
        210             215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Ala Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
        290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

Ile Arg Phe Leu His Ser Phe Thr Met Tyr Lys Leu Tyr Gln Lys Leu
        370                 375                 380

Phe Leu Glu Met Ile Gly Asn Gln Val Gln Ser Val Lys Ile Ser Cys
385                 390                 395                 400

Leu
```